United States Patent [19]
Yang et al.

[11] Patent Number: 5,763,623
[45] Date of Patent: Jun. 9, 1998

[54] PROCESS FOR CATALYTIC EPOXIDATION OF OLEFINIC COMPOUNDS, NOVEL CYCLIC KETONE CATALYSTS USEFUL IN SAID PROCESS

[75] Inventors: Dan Yang; Jian-Hua Zhang, both of Hong Kong; Man-Kin Wong; Yiu-Chung Yip, both of Shatin; Man-Wai Tang, Kwai Chung, all of Hong Kong

[73] Assignee: The University of Hong Kong, Hong Kong, Hong Kong

[21] Appl. No.: 584,604

[22] Filed: Jan. 11, 1996

[51] Int. Cl.$^6$ .................................................. C07D 321/00
[52] U.S. Cl. .................................................. 549/267; 502/172
[58] Field of Search .................................. 549/267; 502/172

[56] References Cited

PUBLICATIONS

Kurihara, M., et al. "Stereoselective Eposidation with Dioxiranes from Generated Ketones", Tet. Let., 35 (10), pp. 1577–1580, Mar. 1994.

Yang, D., et al. "Epoxidation of Olefins Using Methyl(trifluoromethyl)dioxirane Generated in Situ", J. Org. Chem. 60, pp. 3887–3889, Jun. 1995.

Denmark, S.E., et al. "Catalytic Epoxidation of Alkenes wih Oxone ", J. Org. Chem., 60, pp. 1391–1407, Mar. 1995.

*Primary Examiner*—C. Warren Ivy
*Assistant Examiner*—Lyman H. Smith
*Attorney, Agent, or Firm*—Burns, Doane, Swecker & Mathis, L.L.P.

[57] ABSTRACT

Methods for effecting epoxidation of olefinic compounds using cyclic ketone catalysts is provided. In particular, catalytic asymmetric epoxidation of unfunctionalized olefins, e.g., trans-olefins and trisubstituted olefins using novel cyclic ketones possessing $C_2$ symmetric chiral elements is provided.

13 Claims, 2 Drawing Sheets

X-RAY STRUCTURES OF KETONES 1 and 4 (ORTEP VIEW)

X-RAY STRUCTURE OF RACEMIC KETONE 7
(ORTEP VIEW; ONLY ONE MOLECULE IS SHOWN BELOW)

PROCESS FOR CATALYTIC EPOXIDATION OF OLEFINIC COMPOUNDS, NOVEL CYCLIC KETONE CATALYSTS USEFUL IN SAID PROCESS

FIELD OF THE INVENTION

The present invention relates to methods for effecting epoxidation of olefinic compounds using ketone catalysts. More particularly, the present invention relates to catalytic asymmetric epoxidation of unfunctionalized trans-olefins and tri-substituted olefins using cyclic ketone catalysts, preferably $C_2$ symmetric cyclic ketones. The invention is particularly useful for producing optically active epoxides which are important intermediates for synthesis of chiral drugs.

BACKGROUND OF THE INVENTION

Olefinic compounds are hydrocarbon compounds which possess a double bond and which may be represented by the following structure.

Generally, olefinic compounds are characterized based upon their substitution patterns. For example, olefins wherein $R_2$ and $R_3$ are H are referred to as trans-olefins; olefins wherein $R_3$ and $R_4$ are H are referred to as cis-olefins; and olefins wherein $R_4$ is H are called tri-substituted olefins.

Additionally, based on the functional groups present on $R_1-R_4$, olefins can further be classified as functionalized or unfunctionalized olefins. For example, olefins wherein $R_1=CH_2OH$ and which possess a hydroxyl group attached to the allylic position of the double bond, comprise one example of a functionalized olefin. By contrast, olefins wherein $R_1-R_4$ are alkyl and/or aryl groups are referred to as unfunctionalized olefins.

Various methods have been reported in the literature describing means for epoxidation of olefins. For example, Sharpless and his co-workers have reported an effective method for asymmetric epoxidation of functionalized olefins (Katsuki T., Sharpless, B., J. Am. Chem. Soc., 1980, 102, 5974). In their described method, the hydroxyl group in the vicinity of the double bond is able to coordinate to metals and thereby direct the metal oxidant to a particular side of a double bond.

Additionally, epoxidation of unfunctionalized cis-olefins has been reported using chiral Mn-salen complexes which reportedly catalyze asymmetric epoxidation with high enantioselectivity. (See for example Jacobsen, E. N. in Catalytic Asymmetric Synthesis; Ojima, I. Ed., VCH; New York, 1993; Chapter 4.2; Katsuki et al., U.S. Pat. No. 5,420,314).

It has also been reported that dioxiranes are very highly reactive oxidants toward olefins having varying electronic properties (both functionalized and unfunctionalized olefins). For example, dioxiranes have been reported as oxidants for organic reactions such as (1) epoxidation (2) heteroatom oxidation and (3) oxygenation of C—H bonds.

Dioxirane is a three-membered ring cyclic peroxide having the following structure:

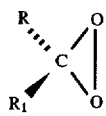

Dioxirane epoxidation occurs in a highly stereo specific manner and occurs efficiently with both electron-rich and electron-deficient donors. For example, only trans-epoxides may be obtained from trans-olefins using dioxirane epoxidation. (For a recent review relating to dioxirane mediated epoxidation see Adam, W.; Hadjiarupoglou, L. P. in Topics In Current Chemistry; Springer-Verlag; Berlin, 1993, Volume 164, page 45 et. seq.). Also, dioxirane epoxidation can be effected catalytically as dioxiranes can be generated in situ from both ketones and oxone (see Curci et al., J. Org. Chem., 1980, 45, 4758; Kurihara et al., Tetrahedron Lett., 1994, 35, 1577; Denmark et al., J. Org. Chem., 1995, 60, 1391; Yang et al., J. Org. Chem., 1995, 60, 3887).

The possibility of using chiral ketones for catalyzing asymmetric epoxidation of unfunctionalized olefins has also been reported in a literature. (See Curci et al., J. Chem. Soc. Chem. Commun., 1984, 155; Curci et al., Tetrahedron Lett., 1995, 36, 5831). However, the reported results have been disappointing. Only low asymmetric induction (below 20% ee) and poor catalytic activity were observed (see Curci et al. Id., 1984 and Curci et al. Id. 1995).

Thus, there still exists a significant need in the art for improved processes and catalysts which provide for epoxidation of olefins. In particular, there exists a significant need for improved methods for catalyzing the asymmetric epoxidation of unfunctionalized trans-olefins and tri-substituted olefins. Moreover, there also exists a need for improved catalysts useful in such processes.

OBJECT OF THE INVENTION

Toward that end, it is an object of the invention to provide novel and improved methods for catalytic epoxidation of olefins.

More specifically, it is an object of the invention to provide novel and improved methods for catalytic asymmetric epoxidation of unfunctionalized trans-olefins and tri-substituted olefins.

It is another specific object of the invention to provide novel cyclic ketones useful for catalytic oxidation, preferably catalytic epoxidation of olefins.

It is a more specific object of the invention to provide novel cyclic chiral ketone catalysts useful for catalytic asymmetric epoxidation of unfunctionalized trans-olefins and tri-substituted olefins.

It is an even more specific object of the invention to provide cyclic ketones containing $C_2$ symmetric elements which catalyze asymmetric epoxidation of unfunctionalized olefins.

It is an even more specific object of the invention to design ketones comprising cyclic analogs of 1,3-diacetoxyacetone and other diacids which possess two-fold symmetry and rigid conformation which catalyze asymmetric epoxidation of unfunctionalized olefins.

It is another object of the invention to provide a novel reaction system which uses homogenous solvent conditions which provide for the efficient catalytic epoxidation of olefins using acyclic and cyclic ketone catalysts.

DETAILED DESCRIPTION OF THE INVENTION

Figure 1:
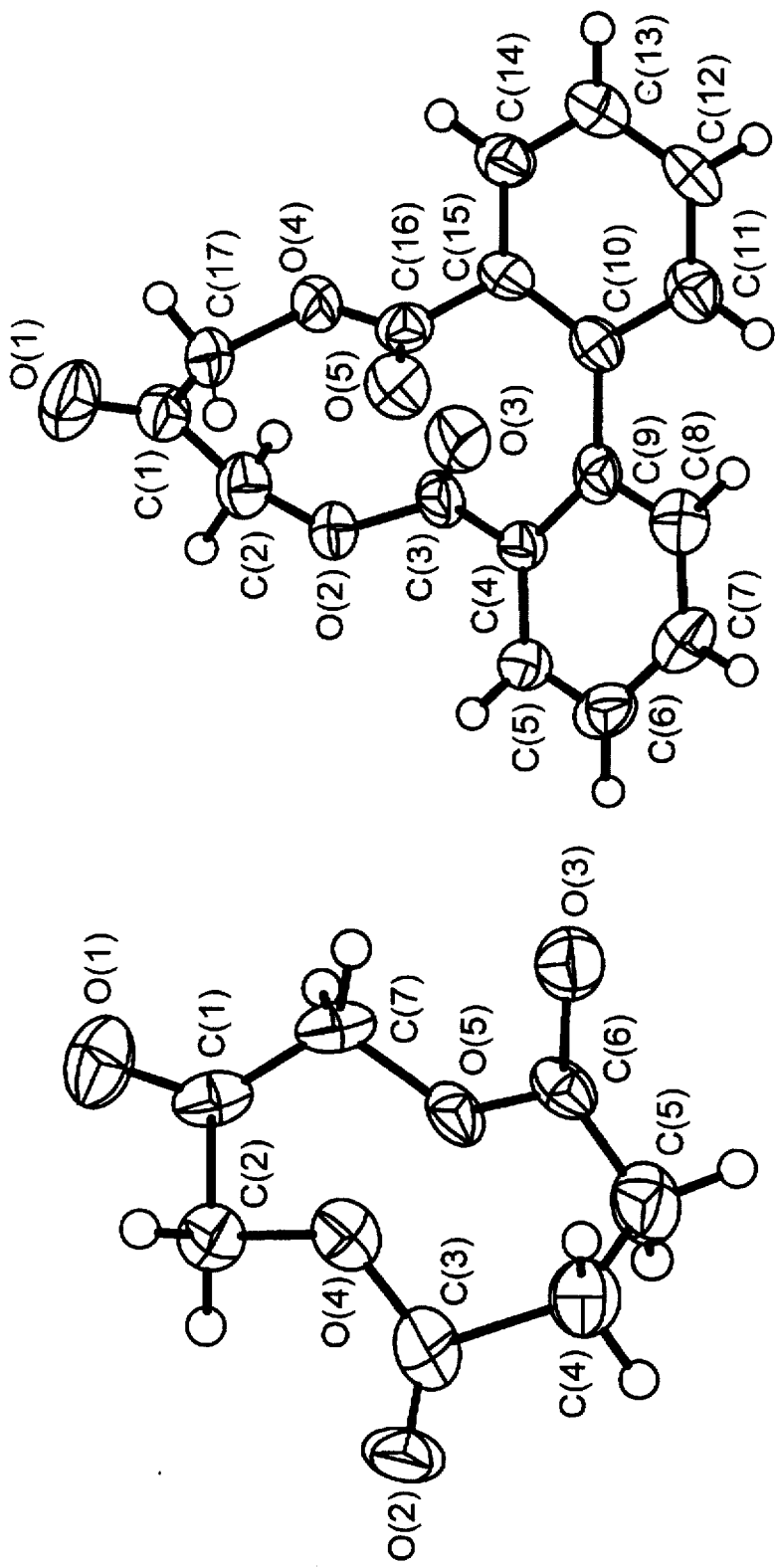
FIG. 1 depicts the X-ray structures of ketones 1 and 4.

As discussed supra, there exists a significant need in the art for improved methods and catalysts for effecting catalytic epoxidation of olefins. More specifically, there exists a need in the art for improved methods and catalysts for effecting catalytic asymmetric epoxidation of unfunctionalized trans-olefins and tri-substituted olefins.

A common structural feature of trans-olefins and tri-substituted olefins is the presence of a large substituent and a small hydrogen atom on one side of a double bond, i.e., $R_2$ versus H. This structure is depicted schematically below:

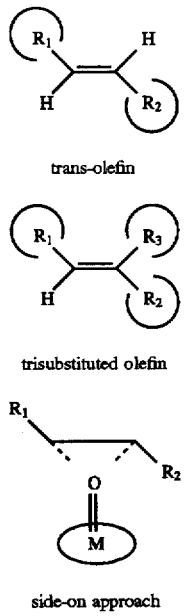

trans-olefin trisubstituted olefin side-on approach

Thus, the key to recognition of these olefins is the requirement for a catalyst which is able to differentiate a large substituent from a hydrogen atom entirely by non-bonded steric interactions. (For examples of successful recognition of trans-olefins and tri-substituted olefins in asymmetric dihydroxylation reactions, see: Sharpless et al, J. Org. Chem., 1992, 57, 2768; Johnson et al, in Catalytic Asymmetric Synthesis Ojima, I., Ed., VCH New York, 1993, Chapter 4.4.) By contrast, for oxo-transfer catalysts carrying planar ligands (such as salen and porphyrin), trans-olefins and tri-substituted olefins are in general poor substrates as suggested by the side-on approach mechanism.

For recent examples of asymmetric synthesis of trans-epoxides from trans-olefins, see Zhang et al, J. Am. Chem. Soc., 1990, 112, 2801; Sakaki et al, Syn. Lett., 1993, 300; Hosoya et al, Syn. Lett., 1993, 641; Groves et al, J. Org. Chem., 1990, 55, 3628; Collman et al, J. Am. Chem. Soc., 1993, 115, 3834, 1993; Collman et al, J. Am. Chem. Soc., 1995, 117, 692. For examples of asymmetric synthesis of trans-epoxides from cis-olefins using chiral Mn-salen catalysts see Lee et al, Tetrahedron Lett., 1991, 32, 6533; Chang et al, J. Am. Chem. Soc., 1994, 116, 6937.

Also, for highly enantioselective epoxidation of conjugated tri-substituted olefins using chiral Mn-salen catalysts, see Brandes et al, J. Org. Chem., 1994, 59, 4378 and for asymmetric epoxidation of tri-substituted olefins catalyzed by enzymes see Allain et al, J. Am. Chem. Soc., 1993, 115, 4415; Koch et al, J. Am. Chem. Soc., 1994, 116, 803.

Recently it was discovered by the present inventors that epoxidation of olefins can be catalyzed efficiently in a homogeneous solvent system comprising acetonitrile and water and using trifluoracetone as a catalyst. (See Yang et al., J. Org. Chem., 1995, 60, 3887, incorporated by reference herein). Given the fact that this reaction occurs under ambient conditions, i.e., at room temperature and is a fairly simple process, this discovery provided a convenient means to compare selected ketones for their ability to catalyze epoxidation reactions.

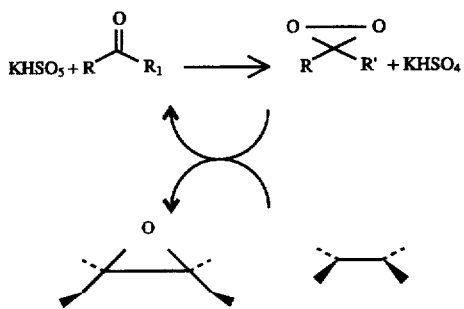

As noted above, previous chiral ketones have resulted in low asymmetric induction (below 20% ee) and have had poor catalytic activity when used to catalyze asymmetric epoxidation of unfunctionalized olefins. However, given that dioxirane epoxidation can function as a catalytic process (because dioxiranes can be generated in situ from ketones and oxone); notwithstanding these previous poor results it was theorized by the present inventors that chiral ketones should still function as ideal catalysts for asymmetric epoxidation.

To ascertain whether this hypothesis was valid, it was first necessary to identify highly efficient ketone catalysts. Assuming that such ketone catalysts could be identified, it was theorized that incorporation of desired chiral elements, that $C_2$ symmetric chiral ketones suitable for catalytic asymmetric epoxidation should be produced. This involved the testing of selected ketones having different structures, and containing various functional groups. Initially, both acyclic and cyclic ketones were tested for their ability to catalyze epoxidation of trans-stilbene. The results obtained are disclosed in Example 1.

In comparing the results obtained using the tested acyclic and cyclic ketones, two general trends were observed by the inventors. First, it was noted that ketones having electron withdrawing groups such as F, Cl and OAc at alpha positions exhibited higher catalytic activity. Secondly, it was observed that ketones exhibiting steric hindrance at alpha positions exhibited decreased activity relative to ketones wherein the alpha position was unrestrained.

Therefore, based on these observations, it was theorized that both steric and electronic factors affect whether a particular ketone will function as an efficient epoxidation catalyst. A similar observation was recently reported by Denmark et al. using a two-phase solvent system (see Denmark et al., J. Org. Chem., 1995, 60, 1391).

As discussed above, it has been reported that dioxirane, functions as a powerful oxidant, and possesses a novel geometry which is believed to render it ideally suited for recognition of trans-olefins and tri-substituted olefins. This structure is set forth below:

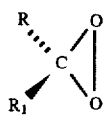

Dioxirane epoxidation follows a concerted and stereo specific pathway. The transition state for oxygen transfer adopts a spiro geometry.

A $C_2$ symmetric chiral dioxirane has a large group and a small group present on each of the two faces (see below).

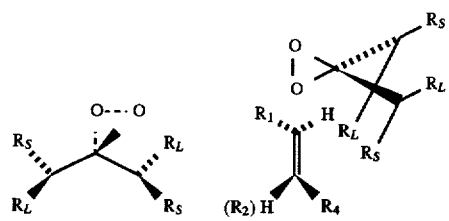

$C_2$ symmetric dioxirane matched orientations in a spiro TS
$R_S$: small substituent; $R_L$: large substituent When encountering trans-olefins and tri-substituted olefins, the $C_2$ symmetric chiral dioxirane prefers the matched orientations which minimize non-bonded steric interactions in the transition state (see above schematic). As a result, oxygen transfer can be restricted to one face of trans-olefins or tri-substituted olefins.

Therefore, based on the results obtained using the tested cyclic ketone catalysts, and the known oxidation activity of dioxiranes, it was theorized that cyclic ketones could be designed which would potentially function as highly effective catalysts for asymmetric epoxidation of unfunctionalized trans-olefins and tri-substituted olefins. Moreover, it was further theorized that in order to provide for effective asymmetric epoxidation, that the designed ketone catalyst should ideally possess $C_2$ symmetry and rigid conformation as dioxiranes have two faces for oxygen transfer.

Based on these assumptions, the present inventors elected to synthesize the following ketones which are set forth which comprise cyclic analogs of 1,3-diacetoxyacetone.

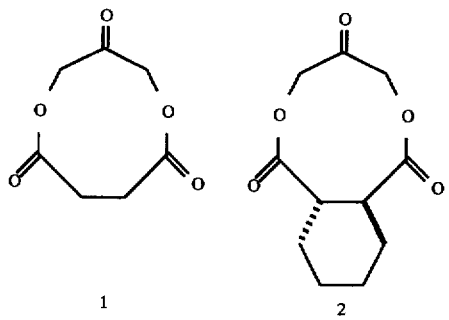

-continued

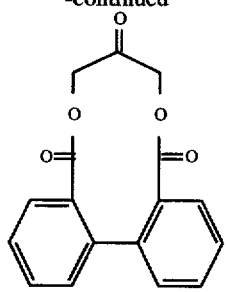

4

It was theorized that these cyclic ketones would possess similar catalytic activity to 1,3-diacetoxyacetone, since ketones possessing two ester substitutions at the alpha position are electronically activated, yet are not sterically hindered. Moreover, ester groups have a strong preference for planar geometry which should further rigidify the conformation of the resultant cyclic ketones. This assumption was also substantiated by a conformational search (a 2,000-step SUMM conformational search) (Goodman, J. M. et al., *J. Comput. Chem.*, 1991, 12, 1110) using MacroModel v4.5 program using MM2* force field which similarly suggested that the above cyclic ketones strongly favor symmetric and rigid conformations.

The above cyclic ketones were prepared from the corresponding diacids and 1,3-dihydroxyacetone. Specifically, ketone 1 above was prepared in two steps using succinic anhydride and 1,3-dihydoxyacetone. Ketones 2 and 4 were prepared in a single step (20–50% yield) using 2-chloro-1-methylpyridinium iodide as a coupling reagent. More detailed procedures used for synthesis and characterization of several of these cyclic ketones may be found in the examples which follow.

It was remarkably found that the x-ray structures of ketones 1 and 4 agreed well with the lowest energy conformations suggested by computer modeling (The RMS deviation of the calculated lowest-energy conformer with the X-ray structure is 0.123 ang atom for ketone 1, and is 0.175 ang/atom for ketone 4.) In the x-ray structures, the carboxyl groups lie on the $C_2$ axis of the molecule; the two ester groups, antiparallel to each other, retain the favorable s-trans geometry and are nearly perpendicular to the macrocyclic ring planes. (See FIG. 1.)

Moreover, it was demonstrated that these cyclic ketones have unprecedented activity in their ability to catalyze epoxidation. This activity was demonstrated based on their ability to catalyze in situ epoxidation of trans-stilbene. The specific reaction conditions are described in the accompanying examples. For example, in a 1:1 ketone/substrate ratio at room temperature, in situ epoxidation of trans-stilbene catalyzed by cyclic ketones 1, 2 and 4 proceeded more rapidly than with trifluoroacetone and acyclic ketone (1,3-diacetoxyacetone). Moreover, epoxides were isolated in almost quantitative yield. Also, the cyclic ketones were stable under the tested reaction conditions and were able to be recovered at high yield without any loss of catalytic activity.

The most efficient of these cyclic ketone catalysts, ketone 4, was selected for further study using other olefinic substrates. (The particular olefinic substrates which were tested are identified in Example 4.) For all of the olefinic substrates tested, ketone 4 showed demonstrably better epoxidation activity than trifluoroacetone. Specifically, epoxidation catalyzed by ketone 4 at room temperature in a 1:1 ketone/substrate ratio occurred more rapidly than with trifluoroacetone at 0° C. in a 10:1 ratio.

Moreover, in order to further confirm the catalytic efficiency of the designed cyclic ketones, epoxidation of trans-stilbene was conducted using one mole percent of ketone 4 at room temperature. Epoxidation was completed in about 12 hours, and trans-stilbene epoxide was recovered at 98% yield.

Given the observed catalytic activities, it is expected that these cyclic ketones as well as cyclic ketones possessing similar structures, will effectively catalyze epoxidation of other olefins, as well as catalyze other oxidation reactions. Moreover, it was further theorized based on these results that ketones 2 and 4, or other cyclic ketones, if a $C_2$ symmetric chiral element were incorporated therein should catalyze asymmetric epoxidation of unfunctionalized olefins, in particular trans-olefins and trisubstituted olefins.

Cyclic ketone 4 was shown to be a highly efficient catalyst for epoxidation; therefore, it was chosen as a starting compound for incorporation of a $C_2$ symmetric chiral element to produce a cyclic ketone catalyst which would potentially catalyze asymmetric epoxidation of both unfunctionalized trans-olefins and tri-substituted olefins.

To determine if the inventors' hypotheses were correct, $C_2$ symmetric chiral ketones were synthesized. It was thereby demonstrated that several $C_2$ symmetric chiral ketones produced using chiral biaryl acids as a starting material provide for efficient asymmetric epoxidation of unfunctionalized trans-olefins and tri-substituted olefins (with 33–94% ee). (See Example 5.)

Given that ketones with chiral centers at their alpha-positions are difficult to synthesize, and are also prone to racemization, the present inventors elected to incorporate the $C_2$ symmetric chiral element in ketone 4 away from the catalytic center, i.e., the keto group contained in the molecule. Initially, it was elected to replace the diphenic unit of ketone 4 with a chiral binaphthalene unit. However, it is expected that other chiral elements may also be incorporated, some of which are identified infra. Incorporation of a chiral binaphthalene structure in ketone 4 results in a $C_2$ symmetric 11-membered ring chiral ketone. The specific cyclic ketone structure is depicted below:

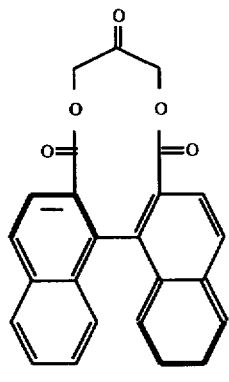

Ketone 7

In the above cyclic ketone structure, (referred to as ketone 7) the two ester groups are believed to function as a conformational rigidifying element as well as functioning as a spacer between the chiral recognition element and the catalytic center. Given this structure, it was hoped that when encountering olefins with large substitutions such as phenyl groups, the chiral element at the remote site should be able to recognize olefinic substitution patterns.

Figure 2:
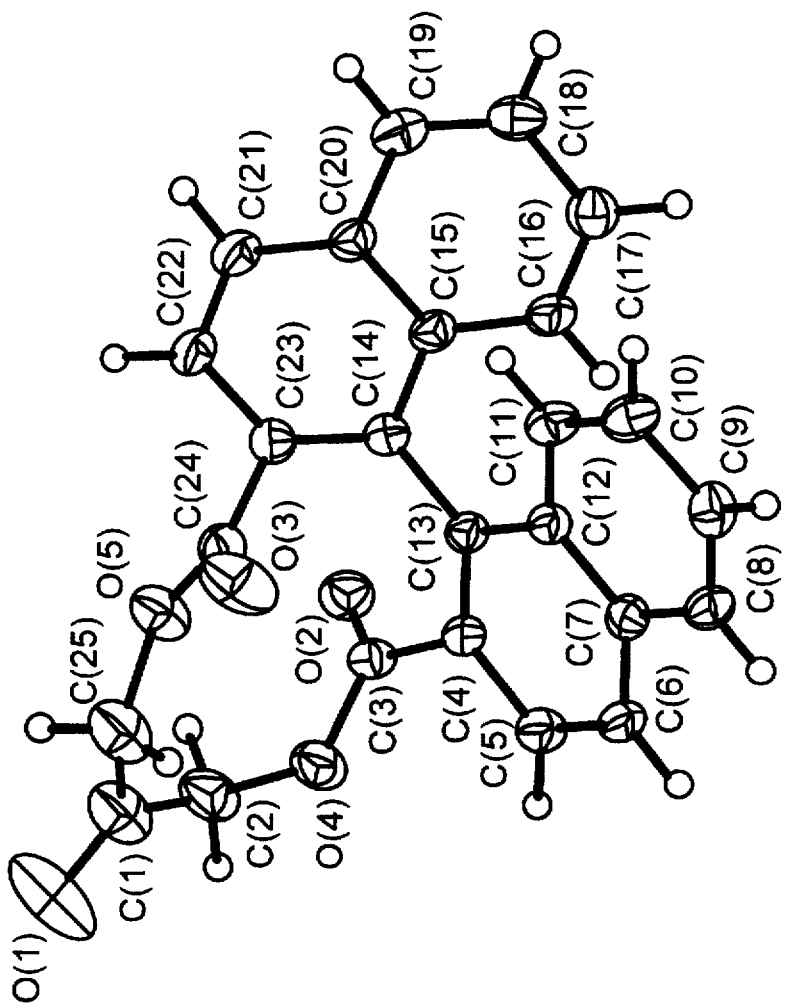
FIG. 2 depicts the X-ray structure of racemic ketone 7.

The design principal on which the subject compounds were synthesized is further substantiated by computer modeling and x-ray analysis. A conformational search suggests that this symmetric chiral cyclic ketone prefers similar conformations to ketone 4, and its lowest energy conformation is almost superimposable with the X-ray structures of racemic ketone 7 (see FIG. 2). In the X-ray structures, the keto group lies on the $C_2$ axis of the molecule; two naphthalene rings point above and below the ring plane with a ca. 70° dihedral angle; the H-3 and H-3' of the two naphthalene rings function as the steric sensor (the distance between H-3 or H-3' and the catalytic center is ca. 5Å). As the calculated C—C(O$_2$)—C bond angle for a dioxirane (117.7°) is approximate to that of a carboxyl group (ca. 120°) it was hoped that the corresponding chiral dioxirane would adopt a similar conformation to this chiral ketone.

This hypothesis has been substantiated by subsequent experiments wherein the subject chiral ketone 7 was used to catalyze asymmetric epoxidation of various trans-olefins and tri-substituted olefins. These experiments and the results obtained are described in Example 5. Similar to ketone 4, epoxidation catalyzed by the chiral ketone 7 was highly efficient with epoxides being obtained in nearly quantitative yield. Moreover, after reaction the chiral ketone catalyst was recovered in excellent yield using flash column chromatography (Yang et al, "A $C_2$ Symmetric Chiral ketone for Catalytic Asymmetric Epoxidation of Unfunctionalized Olefins" (*J. Am. Chem. Soc.*, 1996, in press)) and was recovered without any loss of catalytic efficiency or enantioselectivity.

As hoped the designed chiral ketone gave moderate to good enantioselectivity for epoxidation of trans-olefins and tri-substituted olefins. However, the results obtained were not as favorable for cis-disubstituted olefins or terminal olefins. By contrast, even with 10 mole percent of catalysts, up to 87% ee was obtained for epoxidation of unfunctionalized trans-olefins using chiral ketone 7 as a catalyst. Thus, these results clearly establish that $C_2$ symmetric chiral ketones comprise effective catalysts for asymmetric epoxidation of unfunctionalized trans-olefins and tri-substituted olefins.

As noted, the present inventors initially elected to modify ketone 4 by substitution of the biphenic unit with a chiral binaphthalene structure. However, as $C_2$ symmetric chiral ketones can readily be synthesized from 1,3-dihydroxyacetone as well as other readily available chiral biaryl diacids (such as 6,6'-disubstituted 2,2'-diphenic acids), the chiral environment and the chiral center may easily be modified. For example, chiral ketone 6 was synthesized from chiral 6,6'-dinitro-2,2'-diphenic acid, ad was demonstrated to give the same enantioselectivity as chiral ketone 7 in epoxidation of trans-olefins and tri-substituted olefins. Examples of other $C_2$ symmetric chiral elements include tartaric acid and trans-1,2-cyclohexanedicarboxylic acid, however they are less effective in facilitating asymmetric induction of epoxidation.

Also, based on the structure of ketone 7, it was theorized that an increase in steric bulkiness at H-3 and H-3' positions of this $C_2$ symmetric chiral ketone should result in even better enantioselectivity. This was confirmed by replacing the H-3 and H-3' of the binaphthalene unit of the above chiral ketone with a large substituent, in particular methoxymethyl groups. The resultant ketone 8 indeed provides for better asymmetric induction of epoxidation of many trans-olefins and tri-substituted olefins (52–94% ee, see Example 5 and the accompanying table).

Thus, based on the above, the present invention provides novel methods and cyclic ketone catalysts for epoxidizing olefins, e.g., unfunctionalized trans-olefins and tri-substituted olefins. More particularly, the invention provides cyclic ketone catalysts possessing $C_2$ symmetric chiral elements which catalyze asymmetric epoxidation of unfunctionalized trans-olefins and tri-substituted olefins.

A chiral element refers to any structure not superimposable with its mirror image. A $C_2$ symmetric chiral element refers to chiral elements such that rotation of said chiral elements by an angle of 180° about an axis produces a superposable entity. Therefore, a $C_2$ symmetric chiral ketone is a chiral ketone wherein rotation of the chiral elements by an angle of 180° about the carbonyl axis produces a superposable entity.

The cyclic ketones will preferably possess two-fold symmetry and rigid conformation. Particularly preferred cyclic ketones comprise the cyclic analogs of 1,3-diacetoxyacetone and derivatives thereof.

Preferably, $C_2$ symmetric chiral elements will be incorporated in the molecule away from the catalytic center, i.e. the keto group.

Especially, preferred examples of such chiral ketones will comprise the following generic formula (I) or (II):

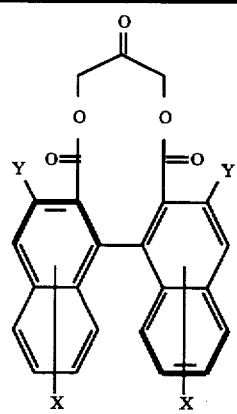

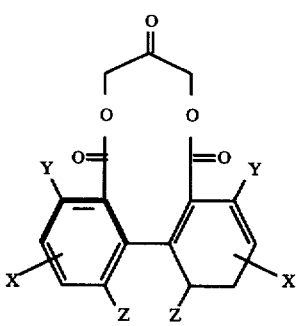

Y = H, $C_1$–$C_4$ alkyl group, aryl group, halogen, $CF_3$, $CF_2CF_3$, COOR', $CR_2OR'$, $CR(OR')_2$ (R = H or alkyl; R' = alkyl), $NO_2$, ON, OTf, OTs, OCOR" (R" = alkyl, $CF_3$, $CF_2CF_3$, aryl), $CR_2Ar$ (R = H or alkyl, Ar = aryl), substituted silyl group
X = H, $C_1$–$C_4$ alkyl group, aryl group, halogen, $CF_3$, $CF_2CF_3$, COOR', $CR_2OR'$, $CR(OR')_2$ (R = H or alkyl; R' = alkyl), $NO_2$, ON, OTf, OTs, OCOR" (R" = alkyl, $CF_3$, $CF_2CF_3$, aryl), $CHAr_2$, $CAr_3$, $CR_2Ar$ (R = H or alkyl, Ar = aryl), substituted silyl group
Z = $C_1$–$C_4$ alkyl group, aryl, $CF_3$, $CF_2CF_3$, Cl, Br, I, $NO_2$, COOR, $CH_2OR$, (R = alkyl), substituted silyl group However, based on the previous description and following examples, it is expected that other cyclic ketones possessing $C_2$ symmetric chiral elements may also be synthesized and used to catalyze epoxidation of unsubstituted olefins, e.g. trans-olefins and tri-substituted olefins. Effective catalysts can readily be identified using suitable solvent reaction condition (acetonitrile/water) and suitable unsubstituted olefin substrates.

The subject cyclic ketones will be used as catalysts during epoxidation of olefins, in particular unfunctionalized olefins such as trans-olefins and trisubstituted olefins. Epoxidation will be effected using solvent conditions which facilitate epoxidation, preferably a homogeneous solvent system such as acetonitrile-water, tetrahydrofuran-water, diethyl ether-water, dioxane-water. Acetonitrite-water solvent systems are preferred. The concentrations thereof may be varied to permit effective solubilization of the ketone and the olefinic substrate.

The reaction will be effected using any olefin, but preferably unfunctionalized trisubstituted olefins or trans-olefins. Such reaction will preferably be effected at room temperature. However, temperatures may be varied, e.g., from about 0° to 40° C. The reaction composition will contain a buffer, e.g., sodium bicarbonate and also an oxidant, e.g., Oxone. The pH of reaction will probably range from about 7 to 8, more preferably from 7 to 7.5.

After reaction, the expoxide will be recovered by suitable methods. Also, the ketone catalyst will preferably be recovered and reused as a catalytic material.

The invention may be further understood based upon the following non-limiting examples.

EXAMPLE 1

The following acyclic and cyclic ketones depicted below were initially compared for their ability to epoxidize trans-stilbene. The results are summarized in Table 1.

TABLE 1

| Entry[a] | Ketones | | | Reaction Time (min)[b] |
|---|---|---|---|---|
| | $R_1$ | $R_2$ | | |
| 1 | $CH_3$ | $CF_3$ | (1a) | 300 |
| 2 | $CH_3$ | $CF_3$ | (1b) | <4 |
| 3 | $CH_3$ | $CH_2F$ | (1c) | 20 |
| 4 | $CH_3$ | $CH_2Cl$ | (1d) | 18 |
| 5 | $CH_3$ | $CH_2OAc$ | (1e) | 30 |
| 6 | $CH_2OAc$ | $CH_2OAc$ | (1f) | 30 |
| 7 | Ph | $CF_3$ | (1g) | 70 |
| | $R_3$ | | | |
| 8 | H | | (2a) | 210 |
| 9 | Cl | | (2b) | 15 |
| 10 | $CH_3$ | | (2c) | >720 |

[a]Reaction conditions: room temperature, 0.1 mmol of trans-stilbene, 1.0 mmol of ketones, 0.5 mmol of Oxone, 1.55 mmol of $NaHCO_3$, 1.5 mL of $CH_3CN$, 1.0 mL of aqueous $Na_2EDTA(4 \times 10^{-4}M)$.
[b]Time when epoxidation was completed as shown by TLC.

EXAMPLE 2

Preparation of trans-Stilbene Epoxide

To an acetonitrile solution (1.5 mL) of trans-stilbene (18 mg, 0.1 mmol) and ketone 4 (29.6 mg, 0.1 mmol) at room temperature was added an aqueous Na₂ EDTA solution (1 mL, 4×10⁻⁴M). To this homogenous solution was added in portions a mixture of sodium bicarbonate (1.55 mmol) and Oxone® (1 mmol). The reaction was finished in 7 min as shown by TLC. The reaction mixture was poured into water (20 mL), extracted with CH₂Cl₂(3×20 mL) and dried with Na₂SO₄. After removal of the solvent under reduced pressure, the residue was purified by flash column chromatography; 20 g of silica gel (Merck, 230–400 mesh) in 100 mL of n-hexane with 2 mL of NEt₃ was poured into a flash column of 20 mm diameter. The column was eluted with n-hexane (50 mL), followed by 5% EtOAc/n-hexane (150 mL) to give trans-stilbene epoxide (19.4 mg, 99% yield), and 40% EtOAc/n-hexane to give ketone 4 (27.6 mg, 93% yield of recovery).

Preparation and Characterization of Ketones

The cyclic ketones identified as 1–8 below were synthesized according to known techniques. The specific methods used to synthesize of ketone 4, 7 and 8 are set forth below.

TABLE 2

Cyclic Ketones Tested as Epoxidation Catalysts

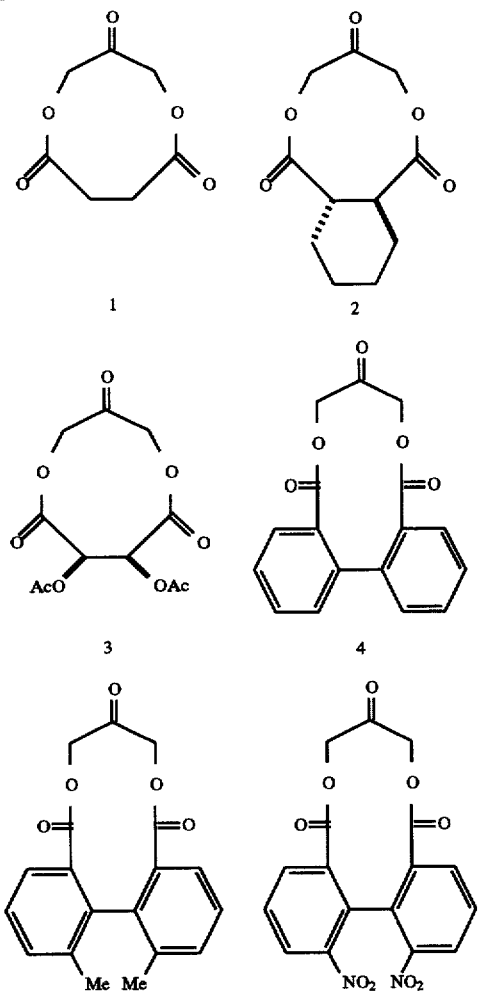

TABLE 2-continued

Cyclic Ketones Tested as Epoxidation Catalysts

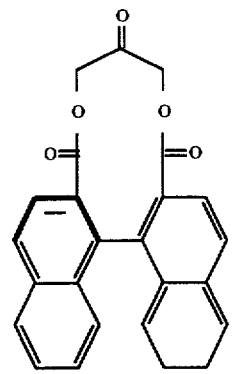

7

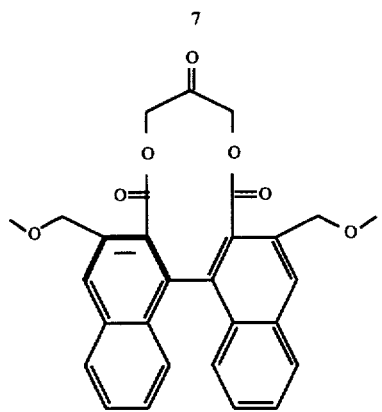

8

Ketone 4

Diphenic acid (121 mg, 0.5 mmol) and 1,3-dihydroxyacetone (67.6 mg, 0.75 mmol) were dissolved in 50 mL of anhydrous acetonitrile. Triethylamine (1.1 mL, 8 mmol) was added to the acetonitrile solution. The resulting solution was stirred at room temperatures for 15 min followed by addition of 2-chloro-1-methylpyridinium iodide (1.022 g, 4 mmol). The reaction mixture was stirred for 12 h under N₂ atmosphere, and then refluxed for 1 h. The solvent was evaporated off under reduced pressure. The dark-brown residue was diluted with CH₂Cl₂ (50 mL). The organic phase was washed with two portions of H₂O (25 Ml), and then dried over Na₂SO₄. Filtration and concentration provided the crude product which was purified by flash chromatography: 30 g of silica gel (Merck, 230–400 mesh) in 200 Ml of n-hexane and 2 Ml of Net₃ was poured into a flash column of 30 mm diameter. The column was eluted (rate=100 mL of solvent per minute) with n-hexane (100 mL), then 35% EtOAc/n-hexane (300 mL) to provide 67 mg (45% yield) of ketone 4 as a white solid: m.p. 166°–167°; Rf0.33 (70:30-hexane;ethyl acetate); ¹H NMR (300 MHz, CDCl₃) δ 7.43–7.65 (m, 8 H, aromatic protons), 5.73 (d, J=15.5 Hz, 2 H), 4.23 (d, J=15.5 Hz, 2 H); ¹³C NMR (75.47 MHz, CDCl₃) δ 202.08, 167.21, 138.76, 132.23, 131.57, 130.56, 127.86, 127.24, 66.81; IR (CCL₄) 1758, 1738, 1479, 1443, 1425, 1344, 1277, 1260, 1237, 1127, 1083 cm⁻¹; MS (EI, 20 eV) m/z 297 (9), 296 (52), 267 (7), 266 (46), 238 (8), 225 (7), 224 (44), 210 (20), 209 (9), 208 (11), 194 (8), 181 (15), 180 (100); HRMS for C₁₇H₁₂O₅ (M⁺), calcd 296.0685, found 296.0683.

Ketone 7

Synthesis and optical resolution of 1,1'binaphthyl-2,2'-dicarboxylic acid was carried out according to the literature procedures: (a) Hall, D. M.; Turner, E. E., *J. Chem. Soc.*, 1955, 1242. (b) Kanoh, S.; Hongoh, Y.; Motoi, M.; Suda, H., *Bull. Chem. Soc. Jpn.*, 1988, 61, 1032.

1,1'-Binaphthyl-2-2'-dicarboxylic acid (171 mg, 0.5 mmol) and 1,3-dihydroxyacetone (67.6 mg, 0.75 mmol) were dissolved in 50 mL of anhydrous acetonitrile. Triethylamine (0.42 mL, 3 mmol) was added to the acetonitrile solution. The resulting solution was stirred at room temperature for 15 min followed by addition of 2-chloro-1-methylpyridinium iodide (306.6 mg, 1.2 mmol). After 5 min, the reaction mixture was refluxed for 12 h under $N_2$ atmosphere, then the solvent was evaporated off under reduced pressure. The brown residue was diluted with $CH_2Cl_2$ (50 mL). The organic phase was washed with 2 portions of $H_2O$ (25 mL), and then dried over $Na_2SO_4$. Filtration and concentration provided the crude product which was purified by flash chromatography: 30 g of silica gel (Merck, 230–400 mesh) in 200 mL of n-hexane and 4 mL of $NEt_3$ was poured into a flash column of 30 mm diameter. The column was eluted (rate=100 mL of solvent per minute) with n-hexane (100 mL), 10% EtOAc/n-hexane (100 mL) and 40% EtOAc/n-hexane (300 mL) to provide 49.5 mg (25% yield) of ketone 7 as a white solid: Rƒ0.26 (70:30-hexane:ethyl acetate); $^1$HNMR (270 MHz, $CDCl_3$) δ 202.15, 167.04, 134.66, 134.00, 132.57, 130.63, 129.12, 128.34, 127.76, 127.62, 127.37, 123.57, 66.96; IR ($CCl_4$) 1760, 1738, 1343, 1275, 1245, 1160, 1131, 1069 $cm^{-1}$; UV-Vis (EtOH) $\lambda$max ($\epsilon$max) 316 (2800), 286 (12300), 222 (96400) nm; MS (EI, 20 eV) m/z 397 (26), 396 (100), 338 (18), 309(9), 308(35), 307(5), 294(6), 280 (16); HRMS for $C_{25}H_{16}O_5$ ($M^+$), calcd 396.0998, found 396.1000.

Ketone 8

The synthetic route for preparation of ketone 8 is shown schematically below in Table 3:

TABLE 3

Synthetic Route for Preparation of Ketone 8

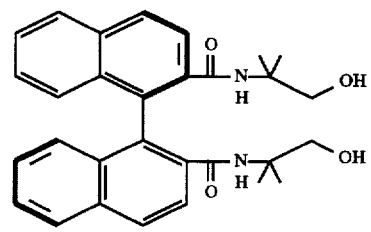

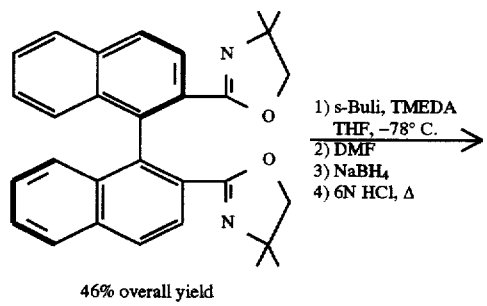

TABLE 3-continued

Synthetic Route for Preparation of Ketone 8

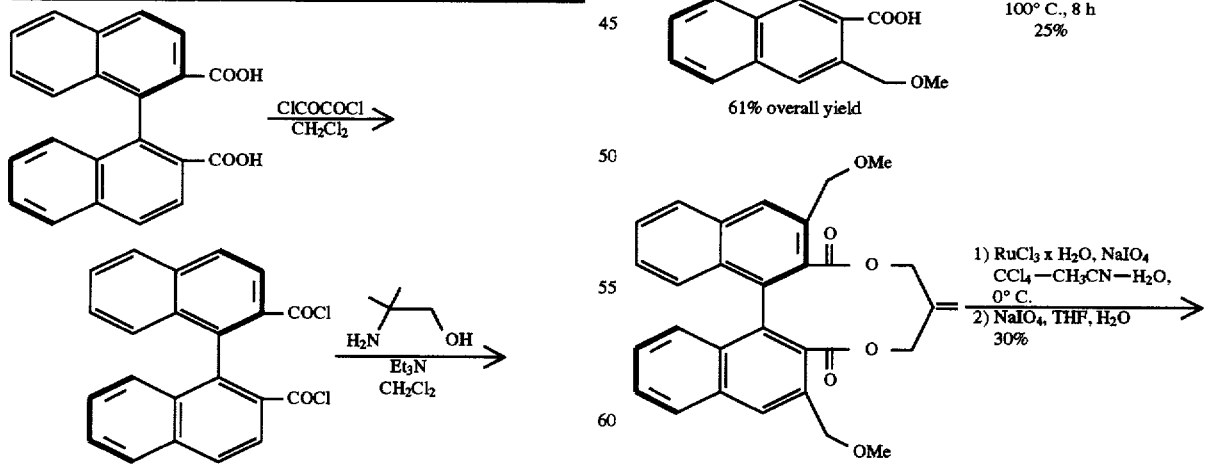

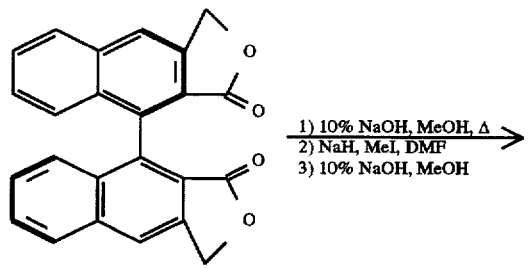

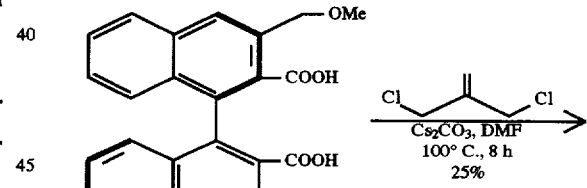

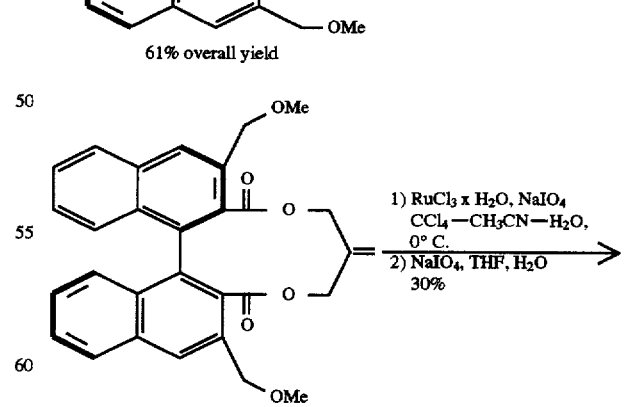

TABLE 3-continued

Synthetic Route for Preparation of Ketone 8

Characterization of ketone 8: $^1$H NMR (300 MHz, CDCl$_3$) δ 7.96 (s,2H), 7.91 (d, J=8.1 Hz, 2H), 7.51 (t, J=7.4 Hz, 2H), 7.25 (t, J =7.4 Hz, 2H), 6.98 (d, J=8.1 Hz, 2H), 4.11 (d, J=15.4 Hz, 2H), 3.38 (s, 6H); $^{13}$C NMR (67.9 MHz, CDCl$_3$) δ 202.73, 166.20, 135.15, 133.26, 132.71, 132.60, 129.44, 128.24, 128.02, 127.66, 127.51, 127.33, 73.70, 66.39 58.32; MS (EI, 20eV) m/e calc'd for C$_{29}$H$_{24}$O$_7$; 484.1522, found 484.1526; 484 (100.00), 452 (61.29), 381 (17.11), 337 (20.44), IR (CH$_2$Cl$_2$) 1760, 1739 cm$^{-1}$.

EXAMPLE 3

The activity of ketones 1–7 was compared for their ability to catalyze the in situ epoxidation of trans-stilbene. Unless otherwise indicated all the epoxidation conditions were carried-out at room temperature, using 0.1 mmol of trans-stilbene, 0.1 mmol of catalyst, 0.5 mmol of oxene, 1.55 mmol of NaHCO$_3$, 1.5 ml of CH$_3$CN and 1.0 mL of aqueous Na$_2$EDTA (4×10$^{-4}$ M)

The results obtained are summarized in the Table 4.

TABLE 4

Activities of Various Ketones in Catalyzing in situ Epoxidation of trans-Stilbene

| Entry | Catalyst | Reaction Time (min) | Epoxide Yield (%)[b] | Ketone Recovery (%) |
|---|---|---|---|---|
| 1 | 1 | 20 | 96 | 30[c] |
| 2 | 2 | 12 | 97 | 80[d] |
| 3 | 3 | 35 | 98 | 29[c] |
| 4 | 4 | 7 | 99 | 93[d] |
| 5[e] | 5 | 10 | 92 | 85[d] |
| 6[f] | 6 | 30 | 97 | — |
| 7[g] | 7 | 20 | 99 | 93[d] |

[b]Isolated yield after flash column chromatography.
[c]Flash column purification without Et$_3$N.
[d]Flash column purification with Et$_3$N.
[e]0.074 mmol of catalyst 5.
[f]0.01 mmol of catalyst 6.
[g]2 mL of CH$_3$CN, 1.7 mL of aqueous Na$_2$EDTA (4 × 10$^{-4}$M).

EXAMPLE 4

The following example compares the ability of cyclic ketone 4 to epoxidize in situ epoxidation of olefinic substrates. The substrates used and the reaction conditions are summarized in Table 5.

TABLE 5

In situ Epoxidation Catalyzed by Ketone 4[a]

| Entry | Substrate | Time | Epoxide Yield (%)[b] | Ketone Recovery[b] (%) |
|---|---|---|---|---|
| 1 | Ph—=—Ph | 7 min | 93 | 91 |
| 2 | Ph—=—Ph | 7 min | 99 | 93 |
| 3[c] | Ph—=—Ph | 45 min | 99 | 98 |
| 4 | H$_3$C—=—Ph (Ph) | 8 min | 98 | 82 |
| 5[d] | cyclohexenyl-Ph | 45 min | 90 | 75 |
| 6 | phenanthrene | 22 min | 80 | 80 |
| 7 | Ph—=—C(O)Ph | 1 h | 96 | 87 |
| 8 | Ph—=—C(O)OCH$_3$ | 2 h | 96 | 82 |
| 9 | F$_3$C-C$_6$H$_4$—=—COOH | 2 h | 85 | 90 |
| 10[e] | naphthoquinone | 6 h | 88 | 81 |

[a]Reaction conditions: 0.1 mmol of substrate, 0.1 mmol of ketone 4, 1.5 mL of CH$_3$CN and 1 mL of aqueous Na$_2$EDTA solution (4 × 10$^{-4}$M).
[b]Isolated yield after flash column chromatography.
[c]0.01 mmol of ketone 4.
[d]0.2 mmol of substrate, 0.2 mmol of ketone 4.
[e]1.5 mL of CH$_3$CN and 2 mL of aqueous Na$_2$EDTA solution (4 × 10$^{-4}$M).

EXAMPLE 5

The following example compares the ability of ketone 7 and ketone 8 to epoxidize unfunctionalized olefins referred to as 9a–9f below, and 10–12.

TABLE 6

Catalytic Asymmetric Epoxidation of Unfunctionalized Olefins

| Entry | Substrate | (R)-7[a] ee (yield) | (R)-8[b] ee (yield) | Epoxide Config. |
|---|---|---|---|---|
| 1 | 9a (R = H) | 47% (91%) | 66% (92%) | (S, S) |
| 2 | 9b (R = Me) | 50% (99%) | 68% (93%) | (S, S) |

TABLE 6-continued

Catalytic Asymmetric Epoxidation of Unfunctionalized Olefins

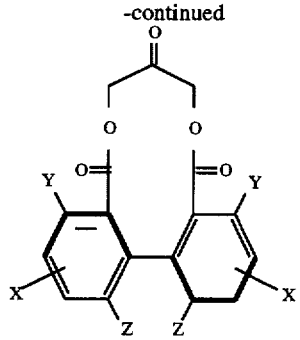

| Entry | Substrate | (R)-7[a] ee (yield) | (R)-8[b] ee (yield) | Epoxide Config. |
|---|---|---|---|---|
| 3 | 9c (R = Et) | 60% (96%) | 76% (94%) | (S, S) |
| 4 | 9d (R = i-Pr) | 71% (98%) | 82% (99%) | (S, S) |
| 5 | 9e (R = t-Bu) | 76% (94%) | 87% (95%) | (S, S) |
| 6 | 9f (R = Ph) | 87% (82%) | 94% (80%) | (S, S) |
| 7 | 10 | 33% (90%) | 52% (93%) | (S, S) |
| 8 | 11 | 50% (98%) | 67% (95%) | (S) |
| 9 | 12 | 33% (83%) | 67% (80%) | (S, S) |

[a]Reaction condition: room temperature, with 0.1 mmol of substrate and 0.01 mmol of (R)-7, 0.5 mmol of Oxone ®, 1.55 mmol of $NaHCO_3$, 1.5 mL of $CH_3CN$ and 1.7 mL of aqueous $Na_2EDTA$ solution ($4 \times 10^{-4}M$).
[b]Reaction condition: room temperature, with 0.1 mmol of substrate and 0.01 mmol of (R)-8, 0.5 mmol of Oxone ®, 1.55 mmol of $NaHCO_3$, 1.5 mL of $CH_3CN$ and 1.0 mL of aqueous $Na_2EDTA$ solution ($4 \times 10^{-4}M$).

These results demonstrate that both of these ketones effectively catalyze epoxidization of unfunctionalized trans-olefins and tri-substituted olefins.

The invention may be embodied in other specific forms without departing from the spirit and scope thereof. Other embodiments are within the claims which follow.

What is claimed is:

1. A method of using $C_2$ symmetric cyclic chiral ketones to catalyze asymmetric epoxidation of unfunctionalized olefin.

2. The method of claim 1 wherein the unfunctionalized olefin is a trans-olefin or tri-substituted olefin.

3. The method of claim 1 wherein the $C_2$ symmetric chiral ketone has generic formula I or II below:

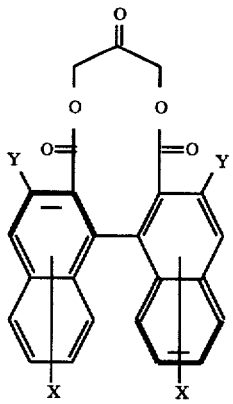

wherein Y is selected from H, $C_1$–$C_4$ alkyl groups, aryl groups, halogen, $CF_3$, $CF_2CF_3$, COOR', $CR_2OR'$, $CR(OR')_2$ (where R=H or alkyl and R'=alkyl), $NO_2$, CN, OTf, OTs, OCOR" (where R"=alkyl, $CF_3$, $CF_2CF_3$ or aryl), $CR_2Ar$ (R=H or Ar=aryl), and substituted silyl groups;

X is selected from the group consisting of H, $C_1$–$C_4$ alkyl groups, aryl groups, halogen, $CF_3$, $CF_2CF_3$, COOR', $CR_2OR'$, $CR(OR')_2$ (R=H or alkyl; R'=alkyl) $NO_2$, CN, OTf, OTs, OCOR" (R"=alkyl, $CF_3$, $CF_2CF_3$, or aryl), $CHAr_2$, $CAr_3$, $CR_2Ar$ (R=H or alkyl, Ar=aryl) and substituted silyl groups; and Z is selected from the group consisting of $C_1$–$C_4$ alkyl group, $CF_3$, $CF_2CF_3$, Cl, Br, I, $NO_2$, COOR, $CH_2OR$ (R=alkyl) and substituted silyl groups.

4. The method of claim 3 wherein said $C_1$–$C_4$ alkyl include methyl, ethyl, normal-propyl, isopropyl, normal-butyl, isobutyl, sec-butyl and tert-butyl and said aryl groups include phenyl, and substituted phenyl, naphthyl and substituted naphthyl groups.

5. The method of claim 1 wherein the ee obtained by epoxidation is at least 30%.

6. The method of claim 1 wherein the epoxidation reaction is effected in a homogeneous solvent system containing acetonitrile and water.

7. The method of claim 1 wherein said asymmetric epoxidation is effected using potassium peroxomonosulfate as an oxidizing agent.

8. The method of claim 1 wherein said asymmetric epoxidation is effected at a pH ranging from about 7 to 8.

9. The method of claim 1 which is effected at a temperature ranging from about 0° C. to about 40° C.

10. The method of claim 9 which is effected at room temperature.

11. The method of claim 8 which is effected using a pH-stat or a buffer.

12. The method of claim 8 wherein said pH preferably ranges from 7 to 7.5.

13. The method of claim 11 wherein said buffer is sodium bicarbonate or sodium hydrogen phosphate.

* * * * *